United States Patent
Bartling et al.

(10) Patent No.: US 8,988,047 B2
(45) Date of Patent: Mar. 24, 2015

(54) METHOD OF CHARGING AN ELECTROCHEMICAL CELL

(75) Inventors: Brandon Alan Bartling, Bethlehem, NY (US); Michael Alan Vallance, Loudonville, NY (US); Richard Louis Hart, Broadalbin, NY (US); David Charles Bogdan, Jr., Scotia, NY (US)

(73) Assignee: General Electric Company, Niskayuna, NY (US)

( * ) Notice: Subject to any disclaimer, the term of this patent is extended or adjusted under 35 U.S.C. 154(b) by 391 days.

(21) Appl. No.: 13/599,469

(22) Filed: Aug. 30, 2012

(65) Prior Publication Data

US 2014/0062412 A1    Mar. 6, 2014

(51) Int. Cl.
*H02J 7/00* (2006.01)
*H01M 10/14* (2006.01)
(Continued)

(52) U.S. Cl.
CPC ............ *H01M 2/0252* (2013.01); *H01M 4/582* (2013.01); *H01M 10/39* (2013.01); *H01M 10/3918* (2013.01); *H01M 10/44* (2013.01); *H01M 2300/0088* (2013.01); *H02J 7/0093* (2013.01)
USPC ........... 320/134; 320/129; 320/130; 320/139; 320/100; 429/52; 340/636.12; 340/636.15; 324/426

(58) Field of Classification Search
CPC ........... H01M 10/14; H01M 6/50; H02J 7/00; H02J 7/04; G08B 21/00; G01N 27/416
USPC ............ 320/134, 129, 130, 139, 100; 429/52; 340/636.12, 636.15; 324/426
See application file for complete search history.

(56) References Cited

U.S. PATENT DOCUMENTS 3,616,315 A * 10/1971 Childs ........................ 205/347
5,508,598 A     4/1996 Al-Abassy
(Continued)

FOREIGN PATENT DOCUMENTS

EP    1076397 A1    2/2001
JP    04026078 A  *  1/1992  ............ H01M 10/48
(Continued)

OTHER PUBLICATIONS

Bones et al.,"Sodium/Iron(II) Chloride Cell with a Beta Alumina Electrolyte", Journal of the Electrochemical Society, Electrochemical Science and Technology, Oct. 1987, 4 pages.
(Continued)

*Primary Examiner* — Phallaka Kik
(74) *Attorney, Agent, or Firm* — Francis T. Coppa (57) ABSTRACT

A method of pulse charging a secondary electrochemical storage cell is provided. The secondary cell includes a negative electrode comprising an alkaline metal; a positive electrode comprising at least one transition metal halide; a molten salt electrolyte comprising alkaline metal haloaluminate; and a solid electrolyte partitioning the positive electrode from the negative electrode, such that a first surface of the solid electrolyte is in contact with the positive electrode, and a second surface of the solid electrolyte is in contact with the negative electrode. The method of charging includes polarizing the cell by applying a polarizing voltage greater than about 0.1 V above the cell's rest potential for a first predetermined period of time; depolarizing the cell for a second predetermined period of time; and repeating the polarizing and depolarizing steps until a charging end-point is reached.

16 Claims, 4 Drawing Sheets

(51) Int. Cl.
*H01M 6/50* (2006.01)
*G08B 21/00* (2006.01)
*G01N 27/416* (2006.01)
*H01M 10/44* (2006.01)
*H01M 2/02* (2006.01)
*H01M 4/58* (2010.01)
*H01M 10/39* (2006.01)

(56) References Cited

U.S. PATENT DOCUMENTS

| | | |
|---|---|---|
| 5,633,574 A | 5/1997 | Sage |
| 5,656,920 A | 8/1997 | Cherng et al. |
| 5,777,453 A | 7/1998 | Imanaga |
| 5,811,890 A * | 9/1998 | Hamamoto ............ 307/66 |
| 5,889,385 A | 3/1999 | Podrazhansky et al. |
| 6,037,751 A | 3/2000 | Klang |
| 6,198,251 B1 | 3/2001 | Landon |
| 6,229,287 B1 | 5/2001 | Ferris et al. |
| 6,307,352 B1 | 10/2001 | Hooper |
| 6,586,940 B2 * | 7/2003 | Asakura et al. ............ 324/426 |
| 7,374,842 B2 | 5/2008 | Ozaki et al. |
| 7,632,604 B2 | 12/2009 | Iacovangelo et al. |
| 8,125,185 B2 | 2/2012 | Takeno |
| 2001/0022518 A1 * | 9/2001 | Asakura et al. ............ 324/426 |
| 2001/0028238 A1 * | 10/2001 | Nakamura et al. ............ 320/132 |
| 2002/0050805 A1 * | 5/2002 | Petrovic ............ 320/130 |
| 2002/0075003 A1 | 6/2002 | Fridman et al. |
| 2004/0008031 A1 * | 1/2004 | Arai et al. ............ 324/429 |
| 2004/0179385 A1 * | 9/2004 | Ogiwara ............ 365/145 |
| 2005/0225299 A1 * | 10/2005 | Petrovic ............ 320/141 |
| 2007/0210746 A1 * | 9/2007 | Tanjou ............ 320/112 |
| 2011/0199055 A1 | 8/2011 | Burchardt et al. |
| 2011/0266998 A1 | 11/2011 | Xiao |
| 2011/0316548 A1 | 12/2011 | Ghantous et al. |
| 2014/0028268 A1 * | 1/2014 | Bourgeois et al. ............ 320/156 |
| 2014/0147772 A1 * | 5/2014 | Xie ............ 429/492 |

FOREIGN PATENT DOCUMENTS

| | | | | |
|---|---|---|---|---|
| JP | 10289733 A | * | 10/1998 | ............ H01M 10/40 |
| JP | 2006012613 A | * | 1/2006 | ............ H01M 10/44 |
| JP | 2008233092 A | * | 10/2008 | ............ G01R 31/36 |

OTHER PUBLICATIONS

Lam et al., "Pulsed-current charging of lead/acid batteries—a possible means for overcoming premature capacity loss?", Journal of Power Sources, Elsevier, 1995, vol. 53, pp. 215-228.

Li et al, "The effects of pulse charging on cycling characteristics of commercial lithium-ion batteries", Journal of Power Sources, Elsevier, 2001, vol. 102, pp. 302-309.

J.L.Sudworth.,"The Sodium/nickel chloride (ZEBRA) battery",Jounrnal of Power Sources, Elsevier, 2001, vol. 100, pp. 149-163.

Jiang et al., "Synergetic Control of Power Converters for Pulse Current Charging of Advanced Batteries From a Fuel Cell Power Source", IEEE Transactions on Power Electronics, Jul. 2004, vol. 19, Np. 4, pp. 1140-1150.

Hussien et al., "Modeling of Sodium Sulfur Battery for Power System Applications", Faculty of Electrical Engineering Universiti Teknologi Malaysia, ELEKTRIKA, 2007, vol. 9, No. 2, pp. 66-72.

"Electric Vehicles", UTC Center for Energy, Transportation and the Environment, Downloaded from the Internet: <http://www.utc.edu/Research/CETE/electric.php>on Aug. 30, 2012, 11 pages.

Podrazhansky et al., "Optimization of Charging Protocol for Efficient Cycling of Li-ion Batteries", ENREV Corp., Downloaded from the Internet:<http://www.electrochem.org/dl/ma/198/pdfs/0059.pdf>on Aug. 30, 2012, 1 page.

* cited by examiner

METHOD OF CHARGING AN ELECTROCHEMICAL CELL

BACKGROUND

The invention relates generally to an electrochemical cell, and in some specific embodiments, to a method of charging an electrochemical cell.

A battery is a component used to store a portion of the energy in mobile systems such as electric vehicles and hybrid electric vehicles (for example locomotives, off-highway mining vehicles, marine applications, buses and automobiles), and for stationary applications such as uninterruptible power supply (UPS) systems and "Telecom" (telecommunication systems). The high-temperature sodium-metal halide electrochemical cells are generally targeted for use in industrial transportation, telecommunication, and uninterruptible power supply (UPS) batteries. These cells could potentially offer high energy density, high power density, longer cell life, and lower cost-requirements for many of these applications.

Normally, a sodium-metal halide battery is made up of many sodium-metal halide cells. Multiple sodium metal halide cells can be connected in series or parallel to form a stack. The current method of charging the sodium metal halide cell can sometimes takes a longer time than desired. In cell operation, it is desirable to minimize the amount of time dedicated to charging the cell, and to maximize the time of delivering energy to the customer. It would therefore be desirable to develop a faster charging method for sodium metal halide cells, without degrading the cell.

BRIEF DESCRIPTION

Some embodiments of the present invention provide a method of pulse charging a secondary electrochemical storage cell. In one embodiment, the secondary cell includes a negative electrode comprising an alkaline metal; a positive electrode comprising at least one transition metal halide; a molten salt electrolyte comprising alkaline metal halo aluminate; and a solid electrolyte partitioning the positive electrode from the negative electrode, such that a first surface of the solid electrolyte is in contact with the positive electrode, and a second surface of the solid electrolyte is in contact with the negative electrode. The method of charging includes polarizing the cell by applying a polarizing voltage greater than about 0.1 V above the cell's rest potential for a first predetermined period of time; depolarizing the cell for a second predetermined period of time; and repeating the polarizing and depolarizing steps, until a charging end-point is reached.

In another embodiment, a method of pulse charging a sodium metal halide cell is provided. The cell includes a negative electrode comprising sodium; a positive electrode comprising nickel chloride; a molten salt electrolyte comprising sodium chloroaluminate; and a solid electrolyte partitioning the positive electrode from the negative electrode, wherein a first surface is in contact with the positive electrode, and a second surface is in contact with the negative electrode. The pulse charging method includes the steps of polarizing the cell by applying a polarizing voltage in a range from about 2.7 V to 3.1 V to the cell for less than about 10 minutes; and then depolarizing the cell, immediately after polarizing, by applying a depolarization current in a range from about 0.01 A to 0.1 A to the cell for less than about 5 seconds; and repeating the polarizing and depolarizing of the cell sequentially, at least 5 times, until a charging end-point is reached.

In one more embodiment, another method of pulse charging a sodium metal halide cell is provided. The cell includes a negative electrode comprising sodium; a positive electrode comprising nickel chloride; a molten salt electrolyte comprising sodium chloroaluminate; and a solid electrolyte partitioning the positive electrode from the negative electrode, wherein a first surface is in contact with the positive electrode, and a second surface is in contact with the negative electrode. The pulse charging method includes the steps of polarizing the cell by applying a polarizing voltage in a range from about 2.7 V to 3.1 V to the cell for less than about 10 minutes; depolarizing the cell, immediately after polarizing, by suspending current flow through the cell for less than about 1 minute; and repeating the polarizing and depolarizing of the cell sequentially at least 5, times until a charging end-point is reached.

In yet another embodiment, an additional method of pulse charging a sodium metal chloride cell is disclosed. The cell includes a negative electrode comprising sodium; a positive electrode comprising nickel chloride; a molten salt electrolyte comprising sodium chloroaluminate; and a beta"-alumina solid electrolyte partitioning the positive electrode from the negative electrode, wherein a first surface is in contact with the positive electrode and a second surface is in contact with the negative electrode. The pulse charging method includes the steps of polarizing the cell by applying a polarizing voltage greater than about 0.15 V above the cell's rest potential until the polarization in the cell is built up to a point wherein an open circuit voltage of the cell is sustainable at a level of greater than about 0.1 V of the cell's rest potential, for about 10 seconds; and then depolarizing the cell immediately after polarizing, by applying a depolarization current in a range from about 0.01 A to 0.1 A to the cell, until the polarization in the cell is reduced to a point wherein an open circuit voltage of the cell for about 10 seconds is less than about 0.1 V above the cell's rest potential; and repeating the polarizing and depolarizing of the cell, until a charging end-point is reached.

DRAWINGS

These and other features, aspects, and advantages of the present invention will become better understood when the following detailed description is read with reference to the accompanying drawings, in which like characters represent like parts throughout the drawings, wherein.

DETAILED DESCRIPTION

Approximating language, as used herein throughout the specification and claims, may be applied to modify any quantitative representation that could permissibly vary, without resulting in a change in the basic function to which it is related. Accordingly, a value modified by a term or terms, such as "about", is not limited to the precise value specified. In some instances, the approximating language may correspond to the precision of an instrument for measuring the value.

In the following specification and claims, the singular forms "a", "an" and "the" include plural referents, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. For example, in some circumstances, an event or capacity can be expected, while in other circumstances, the event or capacity cannot occur. This distinction is captured by the terms "may" and "may be".

As used herein, the term "cathodic material" refers to a material that supplies electrons during charging, and is present as part of a redox reaction. The term "anodic material", as used herein, refers to a material that accepts electrons during charging, and is also present as part of the redox reaction. The cathode volume may include materials having differing functions, including a cathodic material, a support structure, an electrolyte, an electrolyte buffer, and a current collector. The cathodic material is present in the cathode as a participating electrochemical reactant. An electrolyte is a medium that provides the ion transport mechanism between the positive and negative electrodes of a cell, and may act as a solvent for the cathodic material, either in its oxidized form or its reduced form.

Figure 1:
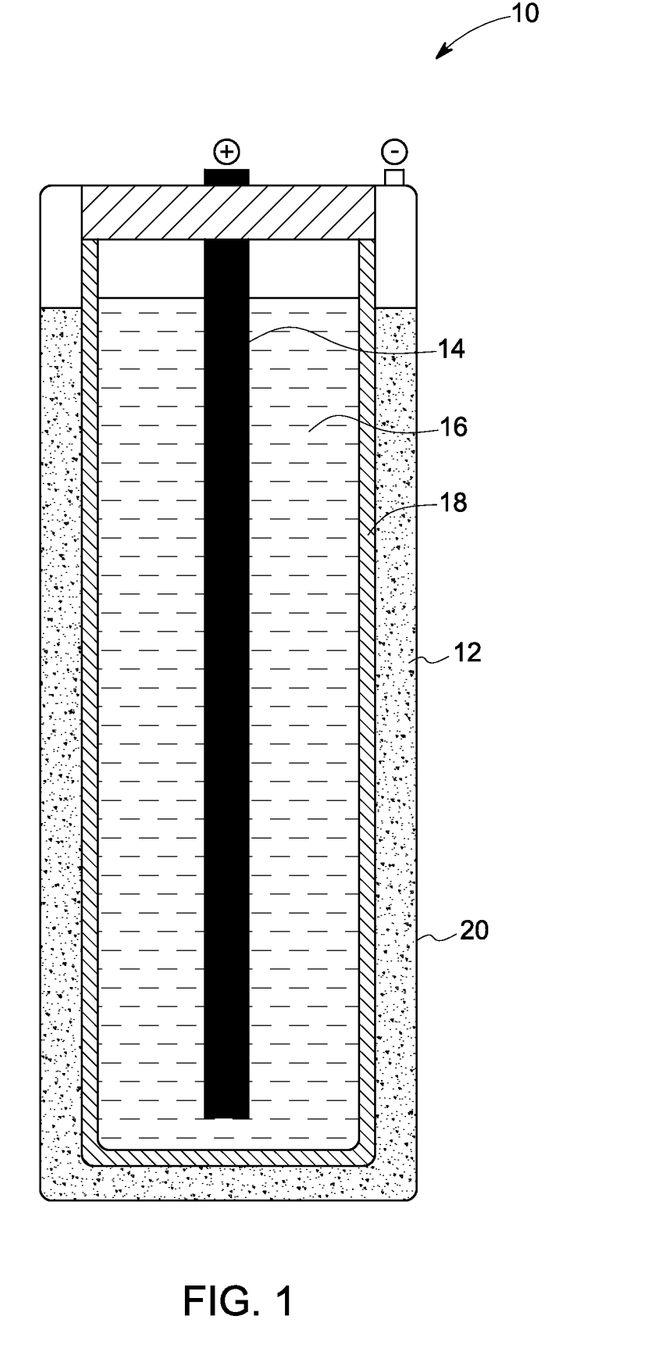
FIG. 1 is a schematic of an electrochemical cell according to an embodiment of the present invention.

FIG. 1 illustrates a schematic of an electrochemical cell 10, according to one aspect of the invention. The electrochemical cell 10 includes an anode chamber 12; a cathode chamber 16 that includes a mixture of cathodic material and electrolyte; and a separator 18. The anode chamber 12 may include a sodium ion source such as, for example, molten sodium. The cathodic material may include transition metals such as nickel, cobalt, and/or iron metals along with their metal halides. The cell 10 further includes a cathode current collector 14 and an anode current collector 20. An excess of solid-state nickel in the cathode chamber 16 may exhibit continuous connectivity and thereby serve as an extended electronic current collector or "electronic grid." The electrolyte may include an ionically conductive sodium metal halide, such as, for example, molten sodium aluminum tetrachloride NaAlCl$_4$. The anode chamber 12 and cathode chamber 16 are separated by a separator 18. The separator 18 is usually a sodium ion-conducting solid electrolyte. Suitable materials for the separator 18 may include beta'-alumina, beta"-alumina, beta'-gallate, beta"-gallate, or zeolite. In specific embodiments, the separator 18 includes a beta"-alumina solid electrolyte (BASE).

In one embodiment, the sodium metal halide cell is manufactured in a discharged state. The cathode compartment is filled with transition metal M (such as, for example, nickel, cobalt, iron, or any combinations of these elements), sodium chloride (NaCl), other optional additives, and a liquid electrolyte. When the sodium battery is first charged by applying a voltage between the anode and the cathode of the cell, sodium ions provided by the dissolution of sodium chloride from the cathode travel through the liquid electrolyte and the separator, and combine with electrons from the external circuit, to form the sodium electrode. The separator is electronically insulating, while at the same time, it is a conductor of sodium ions. When the cell is charged or partially charged, the anode contains liquid sodium. The chloride ions from the dissolution of sodium chloride react with the transition metal in the cathode to form metal chloride, and donate electrons back to the external circuit. The process is reversed during discharge, with sodium ions traveling through the separator to re-form NaCl in the cathode as shown below.

$$MCl_2 \text{ (s)} + 2 \text{ Na (l)} \Leftrightarrow M \text{ (s)} + 2 \text{ Na}^+ + 2Cl^- \qquad (i)$$

The charging of a sodium metal halide cell is traditionally carried out using a constant current charging method, a constant voltage charging method, or using a combination of constant current and constant voltage charging methods. It is desirable to accelerate charging of the sodium metal halide cell to maximize the amount of time when the cell is available to power external electrical loads, while doing so without increasing the cell degradation. Charging the sodium metal halide battery at an increased voltage was observed to decrease the overall charge time. However, the increased voltage charging was further observed by the inventors to degrade the cell faster, compared to using charging voltages below about 0.1 volt (V) of cell over-potential. Cell over-potential is defined as the difference between the applied potential across the positive and negative terminals of a cell, and the rest potential across the terminals of the same cell. As used herein, the "rest potential" of a cell is the open-circuit potential of the cell. Without being bound by any particular theory, the inventors disclose the following mechanism for the cell degradation during faster charging of a sodium metal halide cell, when applying a large over-potential, that is an over-potential greater than about 0.1 V.

In one example, sodium metal chloride cells are chargeable at a temperature at which the sodium aluminum tetrachloride is in the molten state, and a portion of the additional sodium chloride is in the molten state, so as to cause the oxidized cathodic substances (such as for example, transition metals) to be halogenated. In one embodiment, the transition metal chloride species that is present in the charged or partially charged state is insoluble, or minimally soluble, in the molten salt electrolyte. If the transition metal chloride species is insoluble or not mobile, then the microstructure of the positive electrode tends to be stable, and the overall cell degradation tends to be minimal General references to this observation can be found in "A New High Energy Density Battery System" by J Coetzer, *J Power Sources* 18 (1986) 377-380, p 377.

In an example of a sodium chloride containing cell with nickel as the transition metal in the cathode, and with sodium aluminum tetrachloride as the molten salt electrolyte, the electrolyte can be described analytically as a molten mixture of aluminum chloride and sodium chloride. It is found that at the operating temperature range of the cell, the weight fraction of NiCl$_2$ that is soluble in the molten salt electrolyte solution exhibits a minimum value when the aluminum chloride mole fraction in the sodium aluminum tetrachloride is about 0.5. That is, the solubility of the nickel chloride in the sodium aluminum tetrachloride electrolyte is minimum when the sodium chloride to aluminum chloride mole ratio is about 1:1. The solubility of nickel chloride in the solution was found to be increasing when the fraction of aluminum chloride in the electrolyte increases or decreases from the value of about 0.5.

The composition of the molten-salt electrolyte can be said to become acidic when the aluminum chloride concentration in the electrolyte increases from the value of 0.5, and can be said to become basic if the aluminum chloride concentration in the electrolyte decreases from the value of 0.5. In one embodiment, a volume of the porous positive electrode is defined as "acidified" if the analytical mole fraction of aluminum chloride in the electrolyte is greater than 0.505 (molar). The solubility of nickel chloride is notably increased in the acidified electrolyte. Alternatively, the electrolyte becomes saturated with sodium chloride as the aluminum chloride mole ratio is decreased below 0.5. For example at 300 degrees Celsius, the electrolyte becomes saturated with sodium chloride when the aluminum chloride mole ratio is decreased to about 0.493.

It is desirable to maintain the sodium and chloride ion concentrations at a relatively high level, to facilitate the reaction in equation (i) (above), while it is desirable to maintain the nickel ion concentration relatively low. Therefore, it is desirable to operate the electrochemical cell with the aluminum chloride mole fraction in the range between the value at which the sodium chloride concentration is saturated and the value that corresponds to acidification, where nickel ion solubility is high.

The phenomena of solubility dependence on the aluminum chloride concentration in the electrolyte is further found to be applicable to the solubility of iron chloride and cobalt chloride, when iron or cobalt is used as a cathode material.

Without wishing to be bound by any particular theory, it is believed that, during charging, NaCl dissolved in the electrolyte is consumed. In the absence of additional sodium chloride dissolution, or in the case of insufficient sodium chloride distribution, the aluminum chloride ratio increases, and the rest potential of the transition metal electrode (versus a transition metal electrode in a 1:1 electrolyte) rises, relative to the sodium anode, due to decreased sodium chloride chemical activity in the electrolyte. This process is the predominant mechanism of concentration polarization in sodium metal chloride cells. Concentration polarization, by increasing the cell rest potential, decreases the effective cell over-potential, at any given applied cell potential. The effective decrease in effective over-potential reduces the activation over-potential, the fraction of over-potential that is responsible for transferring electrons between the phases. Decreased activation over-potential results in decreased rates of cell charging. Thus, in one embodiment, the solubility of the transition metal chloride is found to be increasing in the electrolyte with the increase in the electrolyte acidification, potentially resulting in degradation, while at the same time, concentration polarization is occurring in the cathode, which reduces the charging performance of the cell.

Further, if the voltage is held constant at an applied over-potential (that is, a value above the rest potential of the cathode), the charging reaction will proceed, until the electrolyte composition acidifies to an appropriate level, so that the concentration over-potential is equal to the applied over-potential. Thus, higher applied potential may cause higher concentration polarization and increased acidification of the cell.

The occurrence of concentration polarization in a sodium metal halide cell further increases the potential that needs to be applied to the cell for charging at any given rate. At a given cell potential, concentration polarization in a cell decreases the ohmic (IR) and activation over-potentials of the cell. The rate of charging goes up with high IR over-potential and high activation over-potential. Therefore, it may be desirable to identify a charging method that reduces concentration polarization, in order to apply a greater IR and activation over-potential to the cell, to drive a faster electrode reaction at a given applied cell potential.

In an exemplary sodium metal halide cell with both nickel and iron metals in the cathode, the rest potentials of the nickel and iron cathodic materials are different. The rest potential of the cell with a nickel cathode is about 2.58 V, and the rest potential with an iron cathode is about 2.35 volts. In such a cell, the primary concern is usually with the polarization concentration that occurs during nickel oxidation, since the iron is oxidized first, when the quantity of available sodium chloride is large enough, so as to minimize polarization concentration during charging of the iron.

Some embodiments of the present invention describe the methods for effective and efficient charging of the sodium metal halide batteries using a pulse charging method. Some aspects of pulse charging of lithium ion batteries and lead acid batteries are known in literature. However, the basis and mechanism for pulse-charging the batteries in the prior art are different from the mechanism for pulse-charging a sodium metal halide battery. In the former cases, the electrolyte degradation of the batteries is a primary consideration, as described below.

In lead acid batteries, an aqueous electrolyte is typically employed; and the water in the electrolyte is electrolyzed to hydrogen and oxygen during continuous charging, leading the cell to dry out. Hence in the lead acid batteries, pulse charging is used to prevent the degradation of electrolyte by dehydration. In lithium ion batteries, normally there is a formation of solid-electrolyte interphase (SEI) on the electrode surfaces. The SEI film deposition normally occurs due to the electromechanical reduction of some species present in the electrolyte. As the SEI becomes thicker, the resistance of the cell increases, and the capacity of the cell is reduced. Therefore, in the lithium ion batteries, the pulse charging is used to control the build-up of the SEI.

Thus, a person skilled in the art will be able to understand that the sodium metal halide batteries are considerably different in their charging and discharging phenomena, when compared to the charging and discharging mechanism of lead acid and lithium ion cells.

In one embodiment, a method of pulse charging a secondary electrochemical storage cell is provided. A secondary electrochemical storage cell is a type of energy accumulator, where the electrochemical reactions are electrically reversible. As used herein, "pulse charging" implies a discontinuous charging, where a voltage or current is applied multiple times to the storage cell before the cell reaches an end-point of charging. The storage cell (hereinafter "cell") is considered as "reaching the end-point of charging" due to multiple conditions. For example, the cell may be termed as reaching the end-point when 1) a targeted amount of capacity has been charged into the cell; 2) a charging current becomes smaller than a pre-set value; 3) a pre-set time is passed; or 4) an event has occurred (such as, for example, a power outage) that requires the cell to discontinue charging, and/or start discharging; or any other circumstance that may be forcing the cell to discontinue charging. In one particular embodiment, the cell is charged until a targeted amount of capacity is incorporated into the cell, and the cell cannot be safely charged any further. In one embodiment, the pre-set value would depend on the size of the cell. For example, in a cell with a capacity of about 45 Ah, the pre-set value may be set in between about 0.1 A and 1 A.

In one embodiment, the cell includes a negative electrode that includes an alkaline metal (sometimes referred to as an "alkali metal"). In one embodiment, the alkaline metal is sodium. The positive electrode may include at least one transition metal halide. The transition metal halide may be chlorides or bromides of nickel, cobalt, iron, or any combinations of these. In one embodiment, the transition metal halide includes nickel chloride. In one specific embodiment, the transition metal halide includes a mixture of nickel chloride and iron chloride. The electrolyte of the cell may include a molten salt that contains alkaline metal haloaluminate. In one embodiment, the electrolyte includes sodium chloroaluminate. In a specific embodiment, the electrolyte comprises $NaAlCl_4$. In one embodiment, the electrochemical cell includes a solid electrolyte that partitions the positive electrode from the negative electrode in the cell. The partition of the cell is such that a first surface of the solid electrolyte is in contact with the positive electrode, and a second surface of the solid electrolyte is in contact with the negative electrode.

In one embodiment, the pulse charging includes a polarizing step and a depolarizing step. A "pulse cycle" may be defined as a combination of one polarizing step and one depolarizing step. In one embodiment, the depolarizing step is carried out immediately after the polarizing step, e.g., less than about 50 milliseconds after polarizing.

In one embodiment, the polarizing step includes applying a polarizing voltage greater than about 0.1 V above the cell's rest potential for a first predetermined period of time. A cell's rest potential is the potential at which the electrochemical cell settles when left undisturbed in the open-circuit condition, and depends on the identity of the anode and cathode pair. In an electrochemical cell including sodium as an anode, the rest potential of the cell is determined by the material of the cathode. For example, as disclosed earlier in the application, in a sodium metal halide cell having nickel metal as the cathode, the rest potential is about 2.58 V at 300 degrees Celsius. Similarly in a sodium metal halide cell having iron as the cathode, the rest potential is about 2.35 V at 300 degrees Celsius.

Applying a polarizing voltage greater than the rest potential of the cell forces the electrochemical reactions of the cell in a particular direction. By convention, positive over-potential is associated with charging (the cathode donates electrons to the external circuit); and a negative over-potential is associated with discharging (the cathode accepts electrons from the external circuit). Higher positive over-potential is associated with faster charging; and more negative over-potential is associated with faster discharging.

The polarizing voltage may be applied to the cell for a first pre-determined period of time. The non-limiting methods of determining the time of polarizing may include the charge build-up on the cell, the concentration over-potential of the cell, and/or the composition of the molten-salt electrolyte. Alternatively, conditions may be found experimentally that provide the best combination of charge acceptance and acceptable rate of degradation. In one embodiment, the polarizing voltage is applied to the cell until the cell becomes slightly acidic, as can be judged by the cell voltage following an interruption of current. For example, if the open-circuit potential after a few seconds remains 0.1 to 0.3 V above the long-term rest potential, the cell is slightly to greatly acidified. In another example, the charge pulse is sustained until a certain fraction of the cell's total charge capacity has been increased. For example, each pulse may contribute about 0.01% to 2% of the cell's capacity.

As disclosed earlier, in one embodiment, the potential applied for polarizing the cell is more than about 0.1V above the rest potential of the cell. In one embodiment, the potential applied is more than about 0.15V above the rest potential of the cell. In a specific embodiment, the potential applied is more than about 0.3V above the rest potential of the cell. In yet another embodiment, the increment of the applied potential above the rest potential of the cell may be more than about 3% of the rest potential. In one embodiment of the invention, the electrochemical cell with a sodium anode may have two active metals, such as, for example, nickel and iron as the cathodic material. In this case, the overall rest potential of the cell may vary with respect to the relative amounts of nickel and iron in the cathode. However, in one embodiment of the invention, when the cell rest potential is considered for calculating the over-potential to be applied to the cell, the rest potential with respect to the active cathode material having the highest rest potential is considered to be the reference point. In one embodiment, the polarizing voltage applied to the cell having a positive electrode including nickel chloride is in a range from about 2.65 V to about 3.2 V. In one particular embodiment, the polarizing voltage is in a range from about 2.7 V to about 3V.

In one embodiment of pulse charging, a sodium metal halide cell is employed, including sodium in the negative electrode; nickel chloride in the positive electrode, sodium chloroaluminate in the molten salt electrolyte; and a solid electrolyte partitioning the positive electrode from the negative electrode. A first surface of the structure is in contact with the positive electrode, and a second surface (as generally depicted in FIG. 1) is in contact with the negative electrode. The polarizing voltage is in a range from about 2.7 V to 3.1 V. In this embodiment, the time duration for applying the polarizing voltage is less than about 10 minutes. In one particular embodiment, the time duration for applying the polarizing voltage is less than about 5 minutes.

Figure 2:
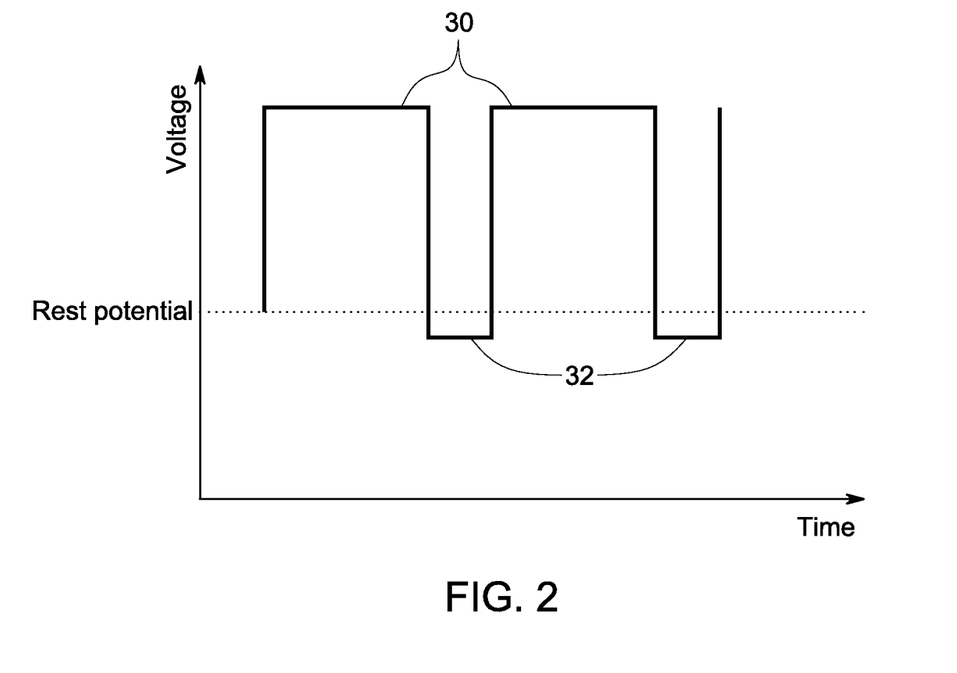
FIG. 2 is a graphical representation of a method of charging an electrochemical cell, according to an embodiment of the invention.
Figure 3:
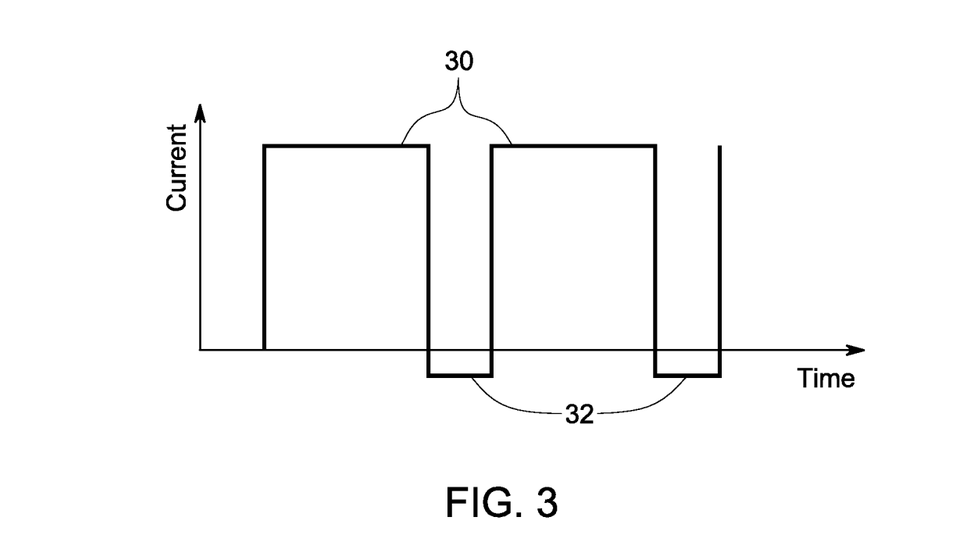
FIG. 3 is a graphical representation of a method of charging an electrochemical cell, according to an embodiment of the invention.
Figure 4:
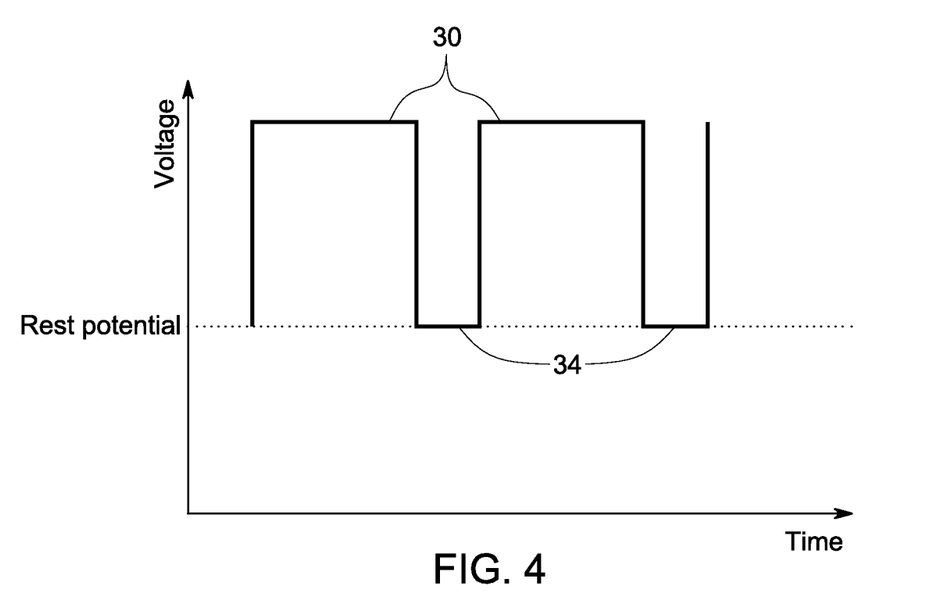
FIG. 4 is a graphical representation of a method of charging an electrochemical cell, according to an embodiment of the invention.
Figure 5:
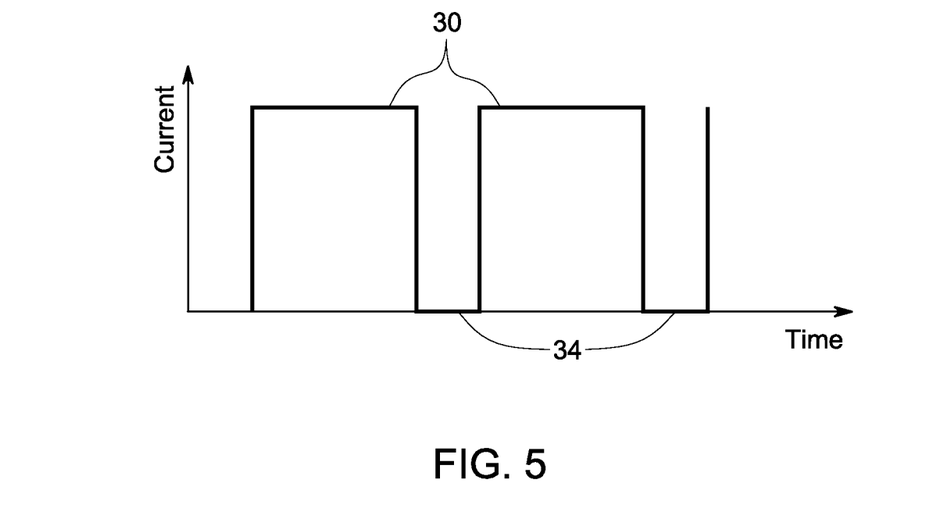
FIG. 5 is a graphical representation of a method of charging an electrochemical cell, according to another embodiment of the invention.

As mentioned hereinabove, the pulse charging of the cell includes a depolarizing step. The depolarizing may be for a second predetermined period of time. In one embodiment, the depolarization step relaxes or depolarizes the concentration polarization that might have built-up in the cell during the polarizing step. The depolarization step may be carried out primarily in two ways. In one technique, after applying the polarization potential to the cell, a relatively small discharge current is applied in the opposite direction of the applied polarizing voltage (in other words, a pulse at a voltage lower than the rest potential is applied to the cell), to depolarize the cell to a small extent. FIG. 2 shows an exemplary voltage distribution during pulse charging of the cell, using a depolarization current for the depolarization step. FIG. 3 shows the current values of the cell during pulse charging in this example. In one example, a depolarization current is applied in the opposite direction to the polarizing voltage, to discharge less than about $\frac{1}{50}^{th}$ of the charge capacity of the cell. In another technique, the voltage application to the cell is cut off for a short time, and the cell is allowed to relax by itself at a time when no external current is applied to the cell, as shown in FIGS. 4 and 5. FIG. 4 shows an exemplary voltage distribution during pulse charging of the cell, using relaxation for the depolarization step. FIG. 5 shows the current values of the cell during pulse charging in this example. (The curves in FIGS. 2-5 are meant to provide a general illustration of the relationship of voltage or current as a function of time, regardless of dimensional units. Exemplary, specific quantities/values are provided elsewhere in this disclosure). Without being bound by any particular theory, it is noted that applying a depolarizing current at an opposite direction of the polarizing voltage preferentially acts to reduce the concentration polarization in those sub-volumes of the cathode where concentration polarization is at a maximum. For example, in a sodium metal chloride cell with nickel chloride in the positive electrode, nickel chloride is readily reduced near the first surface of the separator, where the concentration polarization is greatest. The liberation of chloride ions from the nickel chloride and the flux of sodium ions from the anode act to shift the analytical electrolyte composition toward a ratio of 1:1 aluminum chloride-to-sodium chloride, in the region of the cathode adjacent to the separator.

As disclosed hereinabove, the depolarizing current may be applied to the cell for a second pre-determined period of time. The non-limiting methods of determining the time of depolarizing may be influenced by the charge build-up that had occurred in the cell during the polarizing step, the concentration over-potential of the cell, and/or the composition of the molten-salt electrolyte. In one embodiment, the depolarizing current is applied to the cell until the molten salt electrolyte of the cell becomes nearly equimolar in terms of sodium chloride and aluminum chloride. In one embodiment, the depolarizing current is applied until the molar ratio of the aluminum chloride in the molten salt electrolyte of the cell is less than about 50.5%. In one embodiment, the second predetermined time period for depolarizing the cell by applying a depolarization current is less than about 10 seconds. In a further embodiment, the second predetermined time period is less than about 5 seconds, by applying a depolarization current in a pulse charging cycle.

As disclosed earlier, in one embodiment, the current applied for depolarizing the cell is greater than about 0.01 A after the polarizing step. In one embodiment, the current applied is in a range from about 0.01 A to 0.1 A. In one embodiment, the depolarization current flowing through the cell is much smaller, compared to the current that will be flowing through the cell during polarization. In a particular embodiment, a magnitude of the maximum depolarization current that is passed through the cell is less than about 5% of the maximum current that passed through the cell during the polarization step.

In one embodiment, in a pulse cycle, the depolarization current is applied immediately after cutting off the polarizing voltage as shown in FIG. 2. In one embodiment, the second predetermined time duration for depolarizing by applying a depolarization current is smaller than the first predetermined time duration of applying the polarization voltage. In one embodiment, a ratio of the first predetermined period of time for applying the polarization voltage to the second predetermined period of time for applying a depolarization current is greater than about 100. In some preferred embodiments, the ratio of the first predetermined period of time for applying the polarization voltage to the second predetermined period of time for applying a depolarization current is greater than about 200. In a specific embodiment, this ratio is greater than about 300.

In one embodiment of pulse charging a sodium metal halide cell as described above, the depolarizing current is in a range from about 0.01 A to about 0.1 A. In this embodiment, the time duration for applying the depolarizing current is less than about 5 seconds, and at least about 5 pulse cycles are employed to charge the cell. In some instances the number of pulse cycles depends on the state of charge of the cell. In other words, if the cell is in a less-charged state, a relatively large number of polarizing and depolarizing cycles may be required. However, if the cell is close to being fully-charged, then the number of pulse cycles applied can be reduced.

In one embodiment of pulse charging, the charging of the cell may be achieved by the multiple repetitions of polarizing and depolarizing steps. In one embodiment, the number of pulse cycles required for charging a cell for the maximum capacity is more than about 10. In one embodiment, during a pulse cycle, the pulse pair of one polarizing and one depolarizing step constitutes charging the cell to less than about $1/50^{th}$ of the maximum capacity of the cell.

Considering the method of depolarizing the cell through allowing a cell relaxation by cutting off the applied depolarization current, the relaxation step aids in de-acidifying the cell. For example, in a sodium metal chloride cell with nickel chloride in the positive electrode, when a relaxation step is applied by cutting off all of the external current applied to the cell, the solvated chloride deficit that occurred during polarizing in the positive electrode may be reversed. This can occur because of dissolution of additional sodium chloride into the molten salt electrolyte. Moreover, recirculation currents within the cathode may occur as well, resulting in preferential discharge in acidified portions of the cathode.

As disclosed hereinabove, the relaxation of the cell may be employed for a second pre-determined period of time. The non-limiting methods of determining the time of depolarizing by relaxing the cell may be influenced by the charge build-up that had occurred in the cell during the polarizing step, the concentration over-potential of the cell, and/or the composition of the molten-salt electrolyte. In one embodiment, the depolarizing by relaxation is imposed on the cell until the molten salt electrolyte of the cell becomes nearly equimolar in terms of sodium chloride and aluminum chloride. In one embodiment, the depolarizing by relaxation is imposed until the molar ratio of the aluminum chloride in the molten salt electrolyte of the cell is less than about 50.5%. In one embodiment, the second predetermined time period for depolarizing by relaxation is less than about 2 minutes. In a further embodiment, the second predetermined time period is less than about 1 minute, by relaxing the cell in a pulse charging cycle.

In one embodiment, in a pulse cycle, the depolarizing by relaxation is imposed immediately after cutting off the polarizing voltage, as shown in FIG. 2. In one embodiment, the second predetermined time duration for depolarizing by relaxation is smaller than the first predetermined time duration of applying the polarization voltage. In one embodiment, a ratio of a first predetermined period of time of applying the polarization voltage, to the second predetermined period of time of relaxation. is greater than about 20. In a specific embodiment, this ratio is greater than about 50.

In another embodiment of pulse charging a sodium metal halide cell as described herein, depolarization of the cell is carried out by suspending current flow through the cell, immediately after the polarizing step. In this embodiment, the time duration for suspending the polarizing voltage is less than about 1 minute, and at least about 5 pulse cycles are employed to charge the cell.

In some specific embodiments, the method of pulse charging this type of cell includes the step of polarizing the cell by applying a polarizing voltage greater than about 0.15 V above the cell's rest potential. This polarizing voltage will be applied until such a time that the polarization in the cell is built up to a point where, if an open circuit voltage of the cell was measured, the open circuit voltage remains more than about 0.1 V above the cell's rest potential, at least for a time duration of about 10 seconds. The cell may be depolarized immediately after polarizing, by applying a depolarization current in a range from about 0.01 A to 0.1 A to the cell. This depolarization current may be applied up to a point where, if an open circuit voltage of the cell is measured, the open circuit voltage is less than about 0.1 V above the cell's rest potential for a time duration of about 10 seconds. In certain instances the depolarization current applied may even reduce the cell potential to below the cell's rest potential. The effect of applied depolarization current on the cell's potential may further be influenced by the extent of charge present in the cell at the time of charging. These steps of polarizing and depolarizing may be repeated until a charging end-point of the cell is reached.

EXAMPLE

The following example illustrates a pulse charging method of an electrochemical cell in accordance with exemplary embodiments of the invention, and as such should not be construed as imposing limitations upon the claims.

In an exemplary method of pulse charging a sodium metal chloride cell, the cell is composed of a negative electrode comprising sodium; a positive electrode comprising nickel chloride and iron chloride; a molten salt electrolyte comprising sodium chloroaluminate; and a beta"-alumina solid electrolyte partitioning the positive electrode from the negative electrode, such that a first surface of the solid electrolyte is in contact with the positive electrode, and a second surface of the solid electrolyte is in contact with the negative electrode. The cell was charged using a pulse charging method as described below, and compared to a control charging method at 2.67 V. In the pulse charging method, a polarization pulse of about 0.22V above the rest potential was applied during a polarizing first step; a current of about 1 A was applied for 1 second at the second step, and in a third step, the applied potential was cut off for about 30 seconds. The cell charge resistance was constantly monitored; and the sequence of polarization and depolarization (using depolarization current and relaxation) was repeated multiple times until the cell reached a target cell charge resistance.

Figure 6:
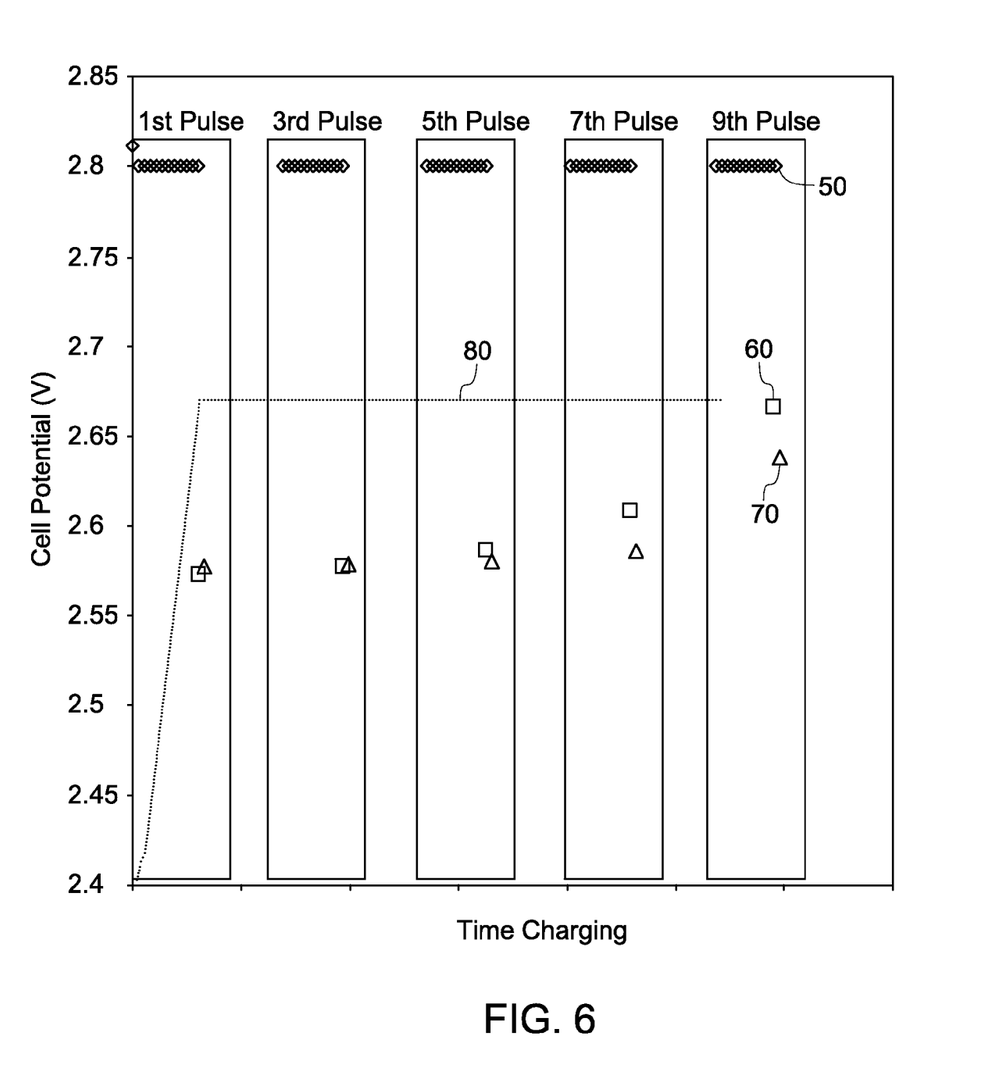
FIG. 6 is a graphical comparison of the pulse charging method with a controlled over-voltage charging.

FIG. 6 shows the cell potential during applied potential 50, depolarization 60 by the application of a depolarizing current, and relaxation 70 steps, compared to the control charging profile 80. In a standard control charging profile 80, the cell was held above the rest potential for a significant portion of the time. By charging for an extended period of time over the rest potential of the cell, the cell was acidified over time. In contrast to the control charging, it was seen that, during the pulse charging protocol, the cell did not reach an acidified state. This is evident by the fact that the cell voltage was staying closer to the rest potential. Only when the cell was nearing the fully charged state, the significant cell voltage rise was observed. This illustrates that the cell is spending a shorter amount of time in an acidified condition, which is beneficial for decreasing the rate of cell degradation.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of pulse charging a secondary electrochemical storage cell, comprising the steps of:
polarizing the cell by applying a polarizing voltage greater than about 0.1 V above the cell's rest potential for a first predetermined period of time;
depolarizing the cell for a second predetermined period of time; and
repeating the polarizing and depolarizing steps until a charging end-point is reached, wherein the cell comprises:
a negative electrode comprising an alkaline metal;
a positive electrode comprising at least one transition metal halide;
a molten salt electrolyte comprising alkaline metal haloaluminate; and
a solid electrolyte partitioning the positive electrode from the negative electrode, wherein a first surface of the solid electrolyte is in contact with the positive electrode, and a second surface of the solid electrolyte is in contact with the negative electrode.

2. The method of claim 1, wherein the alkaline metal haloaluminate comprises sodium chloroaluminate, and the transition metal halide comprises a transition metal chloride.

3. The method of claim 1, wherein the polarizing voltage is at least about 3% greater than a rest potential of the cell.

4. The method of claim 1, wherein a pulse pair of one polarizing and one depolarizing step constitutes charging less than about $\frac{1}{50}^{th}$ of the maximum capacity of the cell.

5. The method of claim 1, wherein the depolarizing step comprises applying a depolarization current greater than about 0.01 A to the cell for the second predetermined period of time.

6. The method of claim 5, wherein a magnitude of the maximum depolarization current is less than about 5% of the maximum current passed through the cell during the polarization step.

7. The method of claim 5, wherein the depolarizing current is applied for a time duration less than about 10 seconds.

8. The method of claim 5, wherein a ratio of the first predetermined period of time to the second predetermined period is greater than about 100.

9. The method of claim 1, wherein the depolarizing step comprises suspending current flow through the cell for the second predetermined period of time.

10. The method of claim 9, wherein the second predetermined period of time is less than about 2 minutes.

11. The method of claim 9, wherein a ratio of the first predetermined period of time to the second predetermined period of time is greater than about 20.

12. The method of claim 1, wherein the positive electrode comprises nickel chloride, and wherein the polarizing voltage is in a range from about 2.65 V to about 3.2 V.

13. The method of claim 12, wherein the polarizing voltage is in a range from about 2.7 V to about 3V.

14. A method of pulse charging a sodium metal halide cell, comprising the steps of:
polarizing the cell by applying a polarizing voltage in a range from about 2.7 V to 3.1 V to the cell for less than about 10 minutes;
depolarizing the cell, immediately after polarizing, by applying a depolarization current in a range from about 0.01 A to 0.1 A to the cell for less than about 5 seconds; and
repeating the polarizing and depolarizing of the cell sequentially at least 5 times, until a charging end-point is reached, wherein the cell comprises:
a negative electrode comprising sodium;
a positive electrode comprising nickel chloride:
a molten salt electrolyte comprising sodium chloroaluminate; and
a solid electrolyte partitioning the positive electrode from the negative electrode, wherein a first surface is in contact with the positive electrode and a second surface is in contact with the negative electrode.

15. A method of pulse charging a sodium metal halide cell, comprising the steps of:
polarizing the cell by applying a polarizing voltage in a range from about 2.7 V to 3.1 V to the cell for less than about 10 minutes;
depolarizing the cell, immediately after polarizing, by suspending current flow through the cell for less than about 1 minute; and repeating the polarizing, and depolarizing of the cell sequentially at least 5 times, until a charging end-point is reached, wherein the cell comprises:
a negative electrode comprising sodium;
a positive electrode comprising nickel chloride;
a molten salt electrolyte comprising sodium chloroaluminate; and
a solid electrolyte partitioning the positive electrode from the negative electrode, wherein a first surface is in contact with the positive electrode and a second surface is in contact with the negative electrode.

16. A method of pulse charging a sodium metal chloride cell that comprises:
a negative electrode comprising sodium;
a positive electrode comprising nickel chloride;
a molten salt electrolyte comprising sodium chloroaluminate; and
a beta"-alumina solid electrolyte partitioning the positive electrode from the negative electrode, wherein a first surface is in contact with the positive electrode and a second surface is in contact with the negative electrode,
said method comprising the steps of:
polarizing the cell by applying a polarizing voltage greater than about 0.15 V above the cell's rest potential until the polarization in the cell is built up to a point wherein an open circuit voltage of the cell for about 10 seconds remains more than about 0.1 V above the cell's rest potential;
depolarizing the cell immediately after polarizing, by applying a depolarization current in a range from about 0.01 A to 0.1 A to the cell until the polarization in the cell is reduced to a point wherein an open circuit voltage of the cell for about 10 seconds is less than about 0.1 V above the cell's rest potential; and
repeating the polarizing, and depolarizing steps until a charging end-point is reached.

* * * * *